US 6,634,268 B1

(12) United States Patent
Guenther et al.

(10) Patent No.: US 6,634,268 B1
(45) Date of Patent: Oct. 21, 2003

(54) METHOD FOR FEEDING A SAMPLE OR CUTTING KNIFE INTO A CUTTING PLANE OF A MICROTOME

(75) Inventors: Bernd Guenther, Neidenstein (DE); Siegbert Holtermueller, Heidelberg (DE); Andreas Laudat, Meckesheim (DE); Rolf Metzner, Dossenheim (DE); Roland Walter, Altlussheim (DE)

(73) Assignee: Leica Microsystems Nussloch GmbH, Nussloch (DE)

( * ) Notice: Subject to any disclaimer, the term of this patent is extended or adjusted under 35 U.S.C. 154(b) by 0 days.

(21) Appl. No.: 09/700,161

(22) PCT Filed: Mar. 8, 2000

(86) PCT No.: PCT/DE00/00727

§ 371 (c)(1), (2), (4) Date: Feb. 1, 2001

(87) PCT Pub. No.: WO00/54020

PCT Pub. Date: Sep. 14, 2000

(30) Foreign Application Priority Data

Mar. 12, 1999 (GB) .......................... 199 11 005

(51) Int. Cl.⁷ .............................. B26D 5/00; G01N 1/06
(52) U.S. Cl. ...................... 83/13; 83/34; 83/36; 83/75; 83/76.8; 83/368; 83/370; 83/703; 83/733; 83/915.5
(58) Field of Search .................. 83/915.5, 13, 34, 83/36, 37, 42, 75, 76, 76.8, 76.9, 171, 351, 353, 367, 368, 370, 705, 703, 613, 733, 734, 403.1, 410.8, 410.9, 411.3, 267, 421

(56) References Cited

U.S. PATENT DOCUMENTS

| 3,191,477 A | * | 6/1965 | Danon ........................... 74/126 |
| 3,611,875 A | * | 10/1971 | Wistedt et al. .............. 409/288 |
| 3,667,330 A | | 6/1972 | Kobernick |
| 4,377,958 A | | 3/1983 | Leighton |
| 4,505,175 A | * | 3/1985 | Reichel ......................... 83/703 |
| 4,532,838 A | * | 8/1985 | Soderkvist ..................... 83/13 |
| 4,691,151 A | | 9/1987 | Behme et al. |
| 5,181,443 A | * | 1/1993 | Sitte et al. ..................... 83/72 |
| 5,226,335 A | * | 7/1993 | Sitte et al. ..................... 83/703 |
| 5,282,404 A | | 2/1994 | Leighton et al. |
| 5,299,481 A | * | 4/1994 | Lihl et al. ..................... 83/170 |
| 5,461,953 A | * | 10/1995 | McCormick .................... 83/36 |
| 5,535,654 A | * | 7/1996 | Niesporek et al. ............. 200/47 |
| 5,609,083 A | * | 3/1997 | Persson ......................... 83/14 |
| 5,671,648 A | * | 9/1997 | Dern .......................... 83/411.1 |
| 5,711,200 A | * | 1/1998 | Thiem ......................... 83/170 |
| 5,752,425 A | * | 5/1998 | Asakura et al. ............... 83/412 |
| 5,761,977 A | * | 6/1998 | Jakobi et al. .................. 83/13 |
| 5,782,572 A | | 7/1998 | Thiem |
| 6,178,757 B1 | * | 1/2001 | Sitte et al. ..................... 62/126 |
| 6,209,437 B1 | * | 4/2001 | Izvoztchikov et al. ......... 83/707 |
| 6,253,653 B1 | * | 7/2001 | Walter et al. .................. 83/703 |
| 6,568,307 B1 | * | 5/2003 | Gunther et al. ............... 83/367 |

FOREIGN PATENT DOCUMENTS

| DE | 35 00 596 A1 | 7/1986 |
| DE | 196 04 001 A1 | 8/1997 |
| WO | WO 91 02960 | 3/1991 |
| WO | WO 91 15746 | 10/1991 |
| WO | WO 98 04898 | 2/1998 |

* cited by examiner

Primary Examiner—Boyer D. Ashley
(74) Attorney, Agent, or Firm—Foley & Lardner

(57) ABSTRACT

A method for cutting sections from a specimen using a microtome wherein a cutting knife or specimen is advanced by an advancing carriage into a sectioning plane of a disk microtome. The advancing carriage is moved by a motor drive in order to bring the specimen into contact with an area sensor. When the specimen comes into contact with the area sensor, the position of the motor drive is determined and is compared with a stored position of the sectioning plane. The stored position is previously determined by manually locating the position drive motor when the specimen contacts the area sensor. Control signals for the motor drive are calculated from the two position values, and the advancing carriage is advanced into the sectioning plane by the motor drive taking these control signals into account.

9 Claims, 1 Drawing Sheet

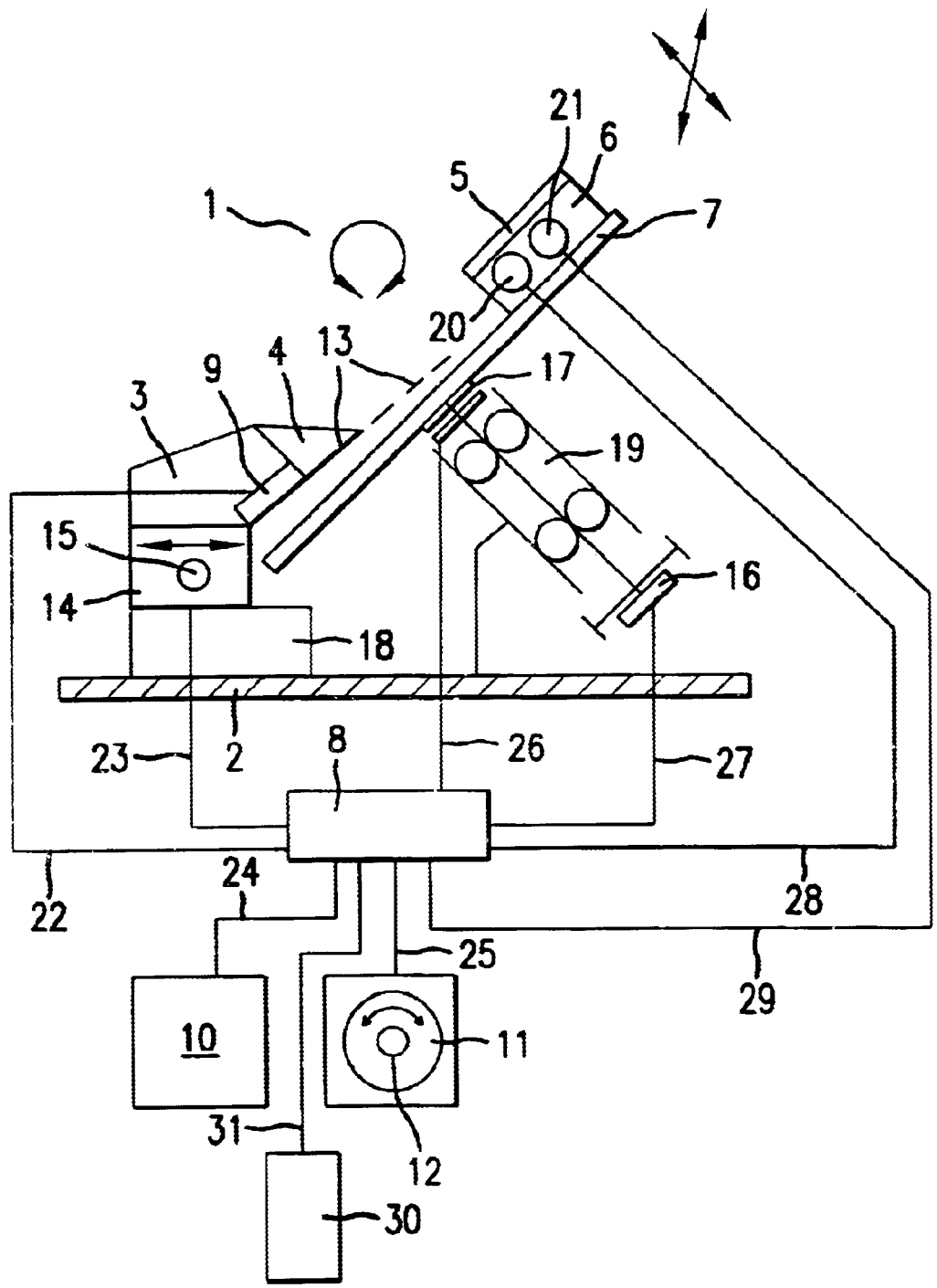

METHOD FOR FEEDING A SAMPLE OR CUTTING KNIFE INTO A CUTTING PLANE OF A MICROTOME

BACKGROUND OF THE INVENTION

The invention relates to a method for advancing a specimen or a cutting knife, by means of an advancing carriage, into a sectioning plane of a microtome, in particular into the sectioning plane of a disk microtome, in which the advancing carriage is moved by means of a motor drive.

A disk microtome is known from WO 98 04 898 A1. To carry out the sectioning, the disk microtome described in this document has a motor drive which is used to produce a relative movement between the object and the cutting knife. Furthermore, the disk microtome is equipped with a motor advancing device for setting the section thickness. Both adjustment motors may be designed as stepper motors and are connected to a control circuit. The motors are controlled by means of the control circuit. An angle-position encoder is provided in the disk microtome for the purpose of detecting the specimen position.

This document leaves open the question of the extent to which the specimen can be advanced substantially automatically into the sectioning plane.

SUMMARY OF THE INVENTION

Therefore, the object of the present invention is to refine a method for advancing a specimen or a cutting knife into the sectioning plane of a microtome in such a way that the specimen is substantially automatically positioned in the sectioning plane.

The method for advancing a specimen or a cutting knife, by means of an advancing carriage, into a sectioning plane of a microtome is distinguished by the fact that the advancing carriage is moved by means of a motor drive and the advancing carriage is initially advanced onto an area sensor. The drive used may, for example, be stepper motors or linear motors with incremental encoder.

When the specimen surface comes into contact with the area sensor, the position of the motor drive is determined and is compared with a stored position of the sectioning plane. Control signals for the motor drive are calculated from the two values, and the advancing carriage is advanced into the sectioning plane by the motor drive, taking these control signals into account.

In a further refinement of the method, to establish the location of the sectioning plane with respect to the location of the area sensor, the advancing carriage is advanced into the sectioning plane under manual control by means of the motor drive. When contact occurs between the specimen surface and the cutting knife, this position of the motor drive is determined. Then the advancing carriage is advanced onto the area sensor by the motor drive and, when the specimen surface comes into contact with the area sensor, the position of the motor drive is determined. The difference between the determined position of the motor drive when it has been advanced into the sectioning plane and the determined position of the advancing carriage when it has been advanced onto the area sensor is formed and stored as the positional value of the sectioning plane. However, it is also possible for the values stored to be not the difference between the two positions, but rather only the position of the sectioning plane, or both positions. It is merely necessary to ensure that the displacement distance for the motor drive from the sensor surface to the sectioning plane can be calculated.

In a further refinement of the invention, while the specimen is being advanced into the sectioning plane by the motor drive, the distance between the stored position of the sectioning plane and the position of the motor drive is determined continuously.

Also, the speed of the motor drive is regulated as a function of the determined distance between the stored position of the sectioning plane and the position of the motor drive. This ensures that the speed of the drive is reduced as the distances between the specimen and the sensor or the sectioning plane become shorter. This may take place continuously or in steps. This ensures that the drive is reliably decelerated in good time before the corresponding position is reached, so that it is prevented from running on, leading to an uncontrolled collision.

In a further refinement of the method, the continuously determined positions of the motor drive are compared with stored positions and, discrete positions coinciding, the speed of the motor drive is reduced and/or the force of the motor-adjustable parameter is increased.

In a further configuration of the invention, the location of the surface of the specimen which is to be sectioned is determined when it comes into contact with the surface of the sensor, and the difference from a stored value for the location of the sectioning plane is formed. By determining the position of the specimen surface, it is possible to achieve automatic alignment, preferably of a specimen which has already been sectioned or a specimen with a smooth surface. This prevents a specimen from being positioned and cut in an inclined position in the sectioning plane.

For this purpose, the specimen surface is aligned with respect to the area sensor by means of a motor-adjustable specimen holder and, in the process, three corners of the specimen successively come into contact with the sensor, and the three-dimensional location of the specimen is calculated from the three positions. Therefore, three corners of the specimen are successively brought into contact with the area sensor and, in the process, the corresponding position of the motor advancing-carriage drive and the positions of the motor-adjustable specimen holder are determined. From these positions, it is then possible to calculate and set a parallel position for the specimen surface with respect to the sectioning plane or the sensor surface.

Naturally, it is also possible for the values for the motor advancing carriage and the stepper motors of the specimen holder to be altered until there is no longer any contact signaled by the area sensor.

In a further configuration, the difference between the three-dimensional location of the specimen and a stored location is calculated, and the motor-adjustable specimen holder is activated as a function of the difference determined.

BRIEF DESCRIPTION OF THE DRAWINGS

The invention is explained in more detail with reference to an exemplary embodiment and with the aid of the diagrammatic drawing.

The FIGURE of drawing is a schematic side view, partly in section, of a microtome according to the invention.

DETAILED DESCRIPTION OF PREFERRED EMBODIMENTS

The FIGURE shows a disk microtome 1 having a supporting bed 2 and a base part 18 of an advancing carriage 14 for a knife holder 3 arranged thereon. The knife holder 3 bears a cutting knife 4. The advancing carriage 5 is designed to be able to move on the base part 18 in the direction indicated by the double arrow and is driven by an advancing stepper motor 15. The sectioning plane 13 is defined by the advancing carriage together with the knife 3. The contact between the cutting edge of the knife and the specimen 5 takes place in this plane 13. The stepper motor 15 is electrically connected to a control circuit 8 via a control line 23. In addition, a pressure-sensitive area sensor 9 is arranged on the knife holder 3. The sensor 9 is connected to the control circuit 8 via a control line 22.

Furthermore, a rotationally movable arm 7, which has a specimen holder 6 which can be aligned in the directions X and Y indicated by double arrows and has a specimen 5 which is to be sectioned arranged on it, is provided on the disk microtome 1. The rotationally movable arm 7 of the disk microtome is mounted in a rotary bearing 19 and is moved by a drive motor 16. The motor 16 is connected to the control circuit 8 via a control line 27. The rotationally movable arm 7 is also assigned an angle encoder 17 which transmits the actual value for the position of the rotationally movable arm 7 to the control device 8 via a control line 26.

The specimen holder 6 which can be oriented in three dimensions is assigned a stepper motor 20 for adjustment in the X direction and a stepper motor 21 for adjustment in the Y direction. Both motors 20 and 21 are connected to the control circuit 8, via in each case one control line 28 and 29.

An external control panel 10 is connected to the control circuit 8 via a control line 24, and a handwheel 11 with an associated encoder 12 is connected to the control circuit 8 via a control line 25.

In the case of the disk microtome, the sectioning is carried out by movement of the rotationally movable arm 7. In the process, the specimen 5 is guided over the cutting knife 4 in the sectioning plane 13. After a section has been made, the advancing carriage 14 is moved forward by the amount corresponding to the section thickness, which has been predetermined via the control panel 10, by means of the control circuit 8.

The positions of the stepper motors 15, 20, 21 and of the angle encoder 17 are continuously checked and compared with stored values in the control circuit 8.

To determine the value for the position of the sectioning plane 13, the distance between the cutting knife 4 or the sectioning plane 13 and the sensor 9, a specimen 5 is initially sectioned under manual control. This is necessary whenever, for example, a knife has been changed or the cutting angle has been altered and the location of the cutting plane 13 has changed. To determine and store the value of the sectioning plane 13, the advancing motor 15 is advanced onto the specimen 5 via switching means on the control panel 10. Once the knife cutting edge 4 and the specimen surface have come into contact with one another, the position of the advancing carriage 14 is stored as a value in the control circuit 8.

Then, the specimen head 6 is positioned in front of the pressure-sensitive sensor 9 and contact is produced between the specimen surface and the sensor 9 by means of the advancing carriage 14. This position of the motor-driven advancing carriage 14 is likewise stored as a value in the control circuit 8. From the difference between the two values, it is possible to calculate the exact distance between the sectioning plane 13 and the sensor 9 as a value (distance). Therefore, after a specimen has been changed, it is possible to make the specimen 5 automatically approach the sectioning plane 13 or to automatically advance the carriage 14 onto the specimen 5. In doing so, the thickness and surface structure of the new specimen 5 to be sectioned is altogether irrelevant. After the distance between the sensor 9 and the sectioning plane 13 has been calculated and has been recorded as a value in the control circuit, it is possible for all further specimens 5 to be positioned automatically. Automatic positioning is effected by producing contact between the specimen 5 and the sensor 9 by means of the motor-driven advancing carriage 14. The value which has been stored in the control circuit 8 is added to this value for the advancing carriage 14. The advancing carriage 14 is automatically moved into the newly calculated position of the sectioning plane 13.

Specimens 5 which have already been sectioned or specimens with a smooth surface can be oriented automatically to the sectioning plane 13. This is achieved in that firstly the specimen holder 6 is moved into a stop position by means of the stepper motors 20 and 21. Then, the motor-driven advancing carriage 14 is used to produce contact between the surface of the specimen 5 and the sensor 9, and this contact is transmitted as a value to the control circuit 8. Then, the stepper motors 20, 21 and the motor-driven advancing carriage 14 are activated in a stepwise manner by means of the control circuit 8 until a signal is no longer emitted by the sensor 9.

However, the specimen 5 may also be oriented in the following way: firstly, both stepper motors 20 and 21 are moved into one of their limit positions by means of the control circuit 8, so as to produce contact with the sensor 9. This and two further corner positions of the surface of the specimen 5 are moved to and stored as values. Through simultaneous recording of the distances covered when moving to the corresponding corner positions allows the orientation of the specimen 15 with respect to the sectioning plane 13 to be calculated and adjusted.

It is possible to dispense with storing the distances involved in moving to the corners if the sensor 9 is designed as a position-sensitive area sensor or a 2D potentiometer pad.

Values for the rotational speed and force of the drive motor 16 are input via the control panel 10 and are stored in the control device 8. The rotational speed and position of the rotationally movable arm 7 can be recorded as a value by means of the connected angle encoder 17 and can be compared with the stored value. The rotational speed is increased and the output of the motor 16 reduced by limiting the current as a function of a defined position when the specimen is situated outside the knife cutting edge 4. While the section is being made, the rotational speed is reduced and the output of the motor 16 is increased again.

However, the rotational speed of the motor 16 may in addition also be controlled via a handwheel 11 which can be operated manually. For this purpose, the signals generated via the encoder 12 when the handwheel 11 is rotated are recorded as values in the control circuit 8 and are compared with the values from the angle encoder 17. A signal for controlling the rotational speed of the motor 16 is obtained from the difference. To start and stop the drive for the disk microtome 1, a foot switch 30 is provided, connected to the control circuit 8 via a control line 31. The foot switch may also be equipped with a potentiometer, the position of which can be used to preset a value for the sectioning speed or the rotational speed of the motor 16 by means of the control circuit 8.

What is claimed is:

1. A method for relatively advancing a specimen with respect to a cutting knife of a microtome to bring the specimen into a sectioning plane of the microtome, comprising:

determining and storing a position of the sectioning plane of the microtome;

initially moving an advancing carriage by means of a motor drive to bring a surface of the specimen into contact with an area sensor;

determining the position of the motor drive at said contact and comparing the determined position of the motor drive with position of the sectioning plane;

generating control signals for the motor drive based on two position values of the stored position of the sectioning plane and the determined position of the motor drive; and advancing the advancing carriage into the sectioning plane by the motor drive as a function of said control signals.

2. A method according to claim 1, wherein said determining and storing the position of the sectioning plane of the microtome comprises determining the location of the sectioning plane with respect to the location of the area sensor by advancing the advancing carriage into the sectioning plane under manual control by means of the motor drive;

when contact occurs between the specimen surface and the cutting knife, determining a contact position of the motor drive;

subsequently advancing the advancing carriage into the area sensor by the motor drive;

when the specimen surface comes into contact with the area sensor, determining the position of the motor drive; and storing the difference between the determined contact position of the motor drive when it has been manually advanced into the sectioning plane and the determined position of the advancing carriage when it has been advanced into the area sensor as the position of the sectioning plane.

3. A method according to claim 2, comprising continuously determining the distance between the stored position of the sectioning plane and the position of the motor drive while the specimen is being advanced by the motor drive.

4. A method according to claim 3, further comprising regulating the speed of the motor drive as a function of the determined distance between the stored position of the sectioning plane and the position of the motor drive.

5. A method according to claim 3, further comprising comparing the continuously determined positions of the motor drive with stored positions and, in the event of the positions coinciding, performing at least one of a reduction of speed of the motor drive and an increase in force of a motor-adjustable parameter.

6. A method according to claim 1, further comprising determining the location of the surface of the specimen which is to be sectioned when it comes into contact with a surface of the sensor, and calculating the difference between this location and the stored value for the location of the sectioning plane.

7. A method according to claim 6, further comprising aligning the specimen surface with respect to the area sensor by means of a motor-adjustable specimen holder by successively bringing three corners of the specimen into contact with the sensor and recording three corner positions, and calculating a three-dimensional orientation of the specimen from the three corner positions.

8. A method according to claim 7, further comprising calculating the difference between the three-dimensional orientation of the specimen and a predetermined stored orientation, and activating the motor-adjustable specimen holder as a function of the difference determined.

9. A method according to claim 1, wherein the specimen is moved into the sectioning plane by a motor-driven arm, and further comprising regulating at least one of the rotational speed and the force of the motor driving said arm as a function of the distance between the specimen and the sectioning plane.

* * * * *